United States Patent [19]

Patel

[11] 4,339,240

[45] Jul. 13, 1982

[54] COLOR CHANGING POLYACETYLENIC COMPOUNDS

[75] Inventor: Gordhanbhai N. Patel, Morris Plains, N.J.

[73] Assignee: Allied Corporation, Morris Township, Morris County, N.J.

[21] Appl. No.: 147,437

[22] Filed: May 7, 1980

[51] Int. Cl.³ ........................................... G01N 21/06
[52] U.S. Cl. ................................. 23/230 R; 116/206; 260/166; 260/177; 260/186; 422/56; 422/57
[58] Field of Search ........................... 422/56, 57, 58; 23/230 R; 252/408; 260/166, 177, 186; 116/206

[56] References Cited

U.S. PATENT DOCUMENTS 3,999,946 12/1976 Patel et al. .............................. 422/56
4,228,126 10/1980 Patel et al. .............................. 422/56

Primary Examiner—Ronald Serwin
Attorney, Agent, or Firm—Alan M. Doernberg; Gerhard H. Fuchs

[57] ABSTRACT

Acetylenic compounds such as 2,6-hexadiyn-1,6-diol-bis(p-phenylazophenylsulfonate) having a conjugated acetylenic portion capable of polymerization on exposure to actinic radiation and thermal annealing and a chromophoric portion. The color of the chromophoric portion provides a background for distinguishing color variations in the initial polymerization of conjugated acetylenic moieties.

24 Claims, 1 Drawing Figure

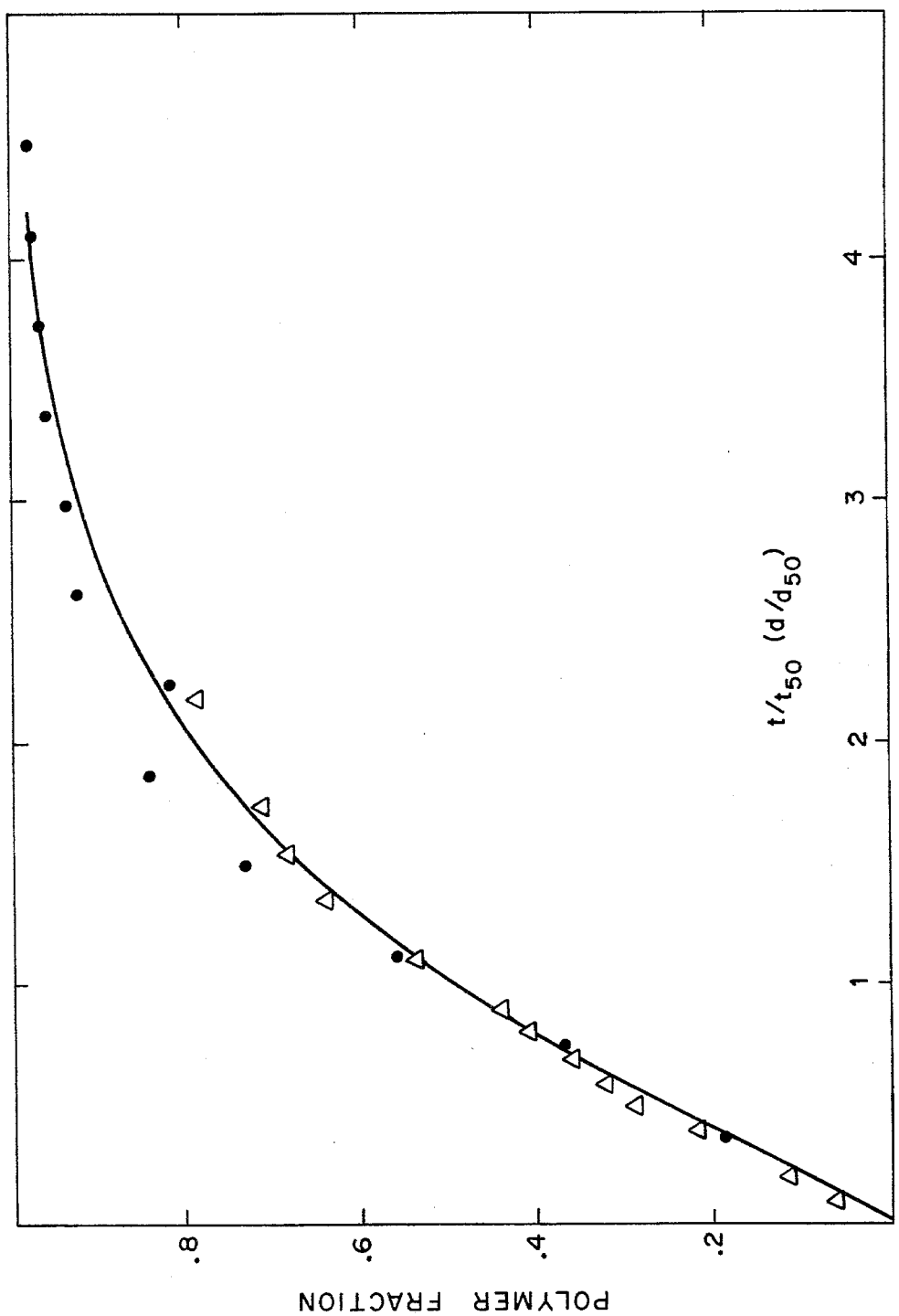

COLOR CHANGING POLYACETYLENIC COMPOUNDS

BACKGROUND OF THE INVENTION

The use of polyacetylenic compounds for time temperature history indicators is described in U.S. Pat. Nos. 3,999,946 and 4,189,399 wherein one or more polyacetylenic compounds such as 2,4-hexadiyn-1,6-bisphenylurethane is coated onto a substrate and thermally annealed at various temperatures. After a period that varies with temperature, a color developed (blue for the above compound, red for other compounds) and eventually the color changed to metallic, at least under gamma ray exposure.

While the above compounds are useful in determining whether or not a fixed amount of time-temperature exposure (or certain radiation exposure) has occurred, they either do not undergo a color change or undergo only one color change, e.g. red to metallic green. Compounds undergoing more than one color change would be desirable to measure variable amounts of exposure.

Accordingly, the present invention contemplates a background color preferably of a differently basic color type than that found on acetylenic polymerization (e.g. yellow when polymerization produces a blue or red color). With this background color variable degrees of polymerizations become visibly detectable.

BRIEF DESCRIPTION OF THE INVENTION

The present invention includes an acetylenic compound having color in the visible spectrum and being active to polymerization on exposure to temperature or actinic radiation comprising an acetylenic portion having at least two conjugated acetylenic unsaturations and being capable of polymerization in the solid state, and at least one chromophore portion absorbing light in the visible spectrum.

Preferred compounds include those of the formula

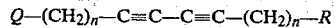
$Q—(CH_2)_n—C≡C—C≡C—(CH_2)_n—R$ wherein at least one of Q and R is a chromophoric substituent absorbing light in the visible spectrum and n is an integer from 1 to 10.

The present invention also includes indicator devices comprising substrates impregnated with such compounds, processes which comprise applying to a perishable product an integral indicator of history of exposure to time-temperature or to radiation comprising at least one such acetylenic compound and perishable products having applied thereto an integral indicator of history of exposure to time-temperature or to radiation comprising at least one such acetylenic compound.

DETAILED DESCRIPTION OF THE INVENTION

The composition of the present invention are used in the same manner as the acetylenic compounds of the U.S. Pat. Nos. 3,999,946 and 4,189,399. They differ therefrom only in having at least one chromophoric substituent absorbing light in the visible spectrum. Thus when the compound is initially applied to a substrate or perishable product, only the chromophoric color is visible. Upon exposure to certain radiation or, in some instances, temperature, a second color develops due to polymerization of the conjugated polyacetylenic groups. It is preferred that these colors differ (e.g. yellow low chromophoric color with blue or red polymerization color, blue chromophoric color with red polymerization color or red chromophoric color with blue polymerization color). with blue polymerization color). This enables gradual changes in the intensity of the polymerization color to be observed as, for example, a yellow substrate goes from yellow (chromophoric color) to increasingly blue shades of green (mixed colors) to blue (dominant polymerization color) and, under proper conditions, to metallic. Such gradiations are easier to differentiate than varying intensities of blue.

The chromophoric substituent may be derived from any conventional chromophore including phthalocyanines, azo, diazo, substituted naphthalenes, anthraquinone derivatives and the like. In general, azo chromphores are preferred. The chromoporic substituent may be linked to the conjugated acetylenic portion in any manner, with ester, sulfonate, urethane and ether linkages being representative. Examples 13-30 illustrate a variety of such compounds which are contemplated in addition to the compounds of Examples 1-8.

Not all such compounds polymerize identically under exposure to temperature or various forms of radiation. Example 12 illustrates the superior behavior of one compound prepared as in Example 1 in the measurement of exposure to temperature or various forms of radiation. This behavior is illustrated in the FIGURE. The compounds of Examples 2-4, 6 and 7 were much less active under thermal exposure and somewhat less active under radiation exposure. The compounds of Examples 5 and 8 were inactive.

The the preferred compounds are of the formula

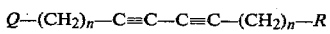
$Q—(CH_2)_n—C≡C—C≡C—(CH_2)_n—R$ where n is an integer of 1 to 10 and Q and R are both chromophoric substituents absorbing light in the visible range, more preferably each azo chromophores, and most preferable

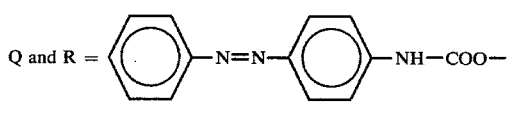

Q and R = or

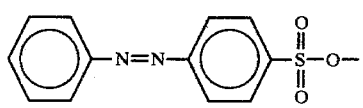

with n preferably 1-4 (especially 2 or 3 with the isocyanate linked group and 1 with the sulfonate linked group).

EXAMPLE 1—1PPAPS

The diacetylenic compound 2,4-hexadiyn-1,6-diol-bis(p-phenylazophenylsulfonate) (hereinafter referred to as "1PPAPS") was prepared from 2,4-hexadiyn-1,6-diol (2.2 g, 0.02 mol) and p-phenylazophenylsulfonyl chloride (1 g, 0.05 mol) as follows. Both reagents and 150 mL of tetrahydrofuran were charged to a three-necked 2000 mL round bottom flask, fitted with an additional funnel and a magnetic stirrer. After cooling to 5° C. with stirring, cold (about 5° C.) KOH solution (11.2 g in 150 mL water) was added dropwise over about 30 minutes. After about 60 more minutes with stirring, cold water was added to precipitate the product 1PPAPS. The product was washed with cold water and methanol. The yield was almost quantitative based on diol charged and the structure was confirmed by elemental and infrared analyses. When the product, coated onto filter paper, was annealed or exposed to ultraviolet radiation or gamma radiation, it changed color as indicated in Table 1.

EXAMPLE 2—2PPAPS

Example 1 was repeated using 0.02 mol of 3,5-octadiyn-1,8-diol as the diol. The structure of the product 3,5-octadiyn-1,8-bis(p-phenylazophenylsulfonate) (called hereinafter "2PPAPS") was confirmed by elemental and infrared analyses. When the product, coated onto filter paper, was thermally annealed or exposed to ultraviolet or gamma radiation, it changed color as indicated in Table 1.

EXAMPLE 3—3PPAPS

Example 1 was repeated using 0.02 mol of 4,6-decadiyn-1,10-diol as the diol. The structure of the product 4,6-decadiyn-1,10-bis(p-phenylazophenylsulfonate) (called hereinafter "3PPAPS") was confirmed by elemental and infrared analyses. When the product, coated onto filter paper, was thermally annealed or exposed to ultraviolet or gamma radiation, it changed color as indicated in Table 1.

EXAMPLE 4—4PPAPS

Example 1 was repeated using 0.02 mol of 5,7-dodecadiyn-1,12-diol as the diol. The structure of the product 5,7-dodecadiyn-1,12-bis-(p-phenylazophenylsulfonate) (called hereinafter "4PPAPS") was confirmed by elemental and infrared analyses. When the product, coated onto filter paper, was thermally annealed or exposed to ultraviolet or gamma radiation, it changed color as indicated in Table 1.

TABLE 1

$$R = \langle\bigcirc\rangle N=N \langle\bigcirc\rangle O-SO_2-(CH_2)_n-$$

| Ex. | n | monomer | initial conversion | partial conversion | final |
|---|---|---|---|---|---|
| 1 | 1 | light pink | gray | blue | metallic |
| 2 | 2 | light pink | orange | red | metallic |
| 3 | 3 | light pink | orange | red | metallic |
| 4 | 4 | light pink | orange | red | metallic |

TABLE 2

$$R = \langle\bigcirc\rangle-N=N-\langle\bigcirc\rangle-NH-CO_2(CH_2)_n-$$

| Ex. | n | monomer | initial conversion | partial conversion | final |
|---|---|---|---|---|---|
| 5 | 1 | yellow | (a) | (a) | (a) |
| 6 | 2 | yellow | orange | red | metallic |
| 7 | 3 | yellow | green | blue | metallic |
| 8 | 4 | yellow | (a) | (a) | (a) |

(a) Inactive, does not polymerize

EXAMPLE 5—1PPAPU

To the same flask as used in Example 1 were charged 5.5 g (0.05 mol) of 2,4-hexadiyn-1,6-diol, 300 mL of tetrahydrofuran, 0.1 g of di-t-butyl-tin-di-2-hexanoate and 2 mL of triethylamine. After stirring for a few minutes, 33.5 g (0.15 mol) of p-phenylazophenyl isocyanate dissolved in 200 mL of tetrahydrofuran was added dropwise over a period of about 30 minutes. The reaction temperature was kept at about 25° C. by a cold water bath surrounding the flask. After 2 hours of reaction, about 1 L of hexane was added. The precipitate was collected by filtration and dried under vacuum. The product 2,4-hexadiyn-1,6-bis(p-phenylazophenylurethane) (hereinafter called "1PPAPU") was determined to have been produced in essentially quantitative yields (based on diol) and its structure was confirmed by elemental and infrared analyses. Its behavior upon coating onto filter paper, upon thermal annealing and exposure to ultraviolet or gamma radiation is indicated in Table 2.

EXAMPLES 6-8—2PPAPU, 3PPAPU, 4PPAPU

In like manner to the method of Example 5, 3,5-octadiyn-1,8-bis-(p-phenylazophenylurethane) (hereinafter called "2PPAPU"); 4,6-decadiyn-1,10-bis(p-phenylazophenylurethane) (hereinafter called "3PPAPU") and 5,7-dodecadiyn-1,12-bis(p-phenylazophenylurethane) (hereinafter called "4PPAPU") were prepared by substituting 0.15 mol of the diols used in Examples 2, 3 and 4 for the diol used in Example 5. The structures of the products were confirmed by elemental and infrared analyses. The behavior of each product after coating onto filter paper, upon thermal annealing and exposure to ultraviolet or gamma radiation is indicated in Table 2.

EXAMPLE 9—REFLECTANCE SPECTRA OF 1PPAPS

The PPAPS prepared according to Example 1 was coated onto several pieces of filter paper from about one percent solution and they were heated to about 90° C. (plus or minus 2° C.). The reflectance spectra were taken over the visible range with a Perkin-Elmer UV-visible spectrophotometer (Model 200) as described by G. N. Patel et al. in *J. Am. Chem. Soc.*, vol. 102, p. 461 (1980). The intensity of reflectance peaks at about 460 nm The intensity of reflectance peaks at about 460 nm and 370 nm remained essentially unchanged among samples with different exposure times or no exposure. A peak at 595 nm, not present in the unexposed sample, appeared with increasing intensity over increasing exposure time.

EXAMPLE 10—REFLECTANCE SPECTRA OF 3PPAPS

Example 9 was repeated using 3PPAPS instead of 1PPAPS. Again, peaks at about 460 nm and 240 nm were essentially unchanged by comparison of samples with no exposure time or varying exposure time. A peak at about 520 nm, not present in the unexposed sample, appeared with increasing intensity as the exposure time increased.

EXAMPLE 11—REFLECTANCE SPECTRA OF 3PPAPU

Example 9 was repeated using 3 PPAPU instead of 1PPAPS. Again, peaks at about 460 nm and 420 nm were essentially unchanged by comparison of samples with no exposure time or varying exposure time. A peak at about 620 nm, not present in the unexposed sample, appeared with increasing intensity as the exposure time increased.

EXAMPLE 12—POLYMERIZATION RATE OF 1PPAPS

Unlike the materials of Example 2-8, 1PPAPS appears to polymerize quantitatively either upon thermal annealing or upon exposure to high energy radiation (e.g. ultraviolet or gamma radiation). Its polymerization rate was faster under similar conditions than any other diacetylene heretofore tested including 2,4-hexadiyn-1,6-bis-(p-toluenesulfonate) (hereinafter called "PTS"). Most diacetylenes (including those of Examples 2-8) polymerize only to about ten percent upon thermal annealing, higher upon gamma ray irradiation. The unique behavior of PTS is sometimes referred to as "autocatalytic" in the sense that the reaction is initially slow followed by very fast, relatively complete reaction. 1PPAPS showed a fast, linear reaction rate followed by a slow, asymptotic reaction rate.

BRIEF DESCRIPTION OF THE DRAWING

The FIGURE is a graphic view of polymerization under various conditions, as described in Example 12.

γ-RAY POLYMERIZATION

About 0.5 g of 1PPAPS was irradiated with $Co^{60}$ gamma-rays at room temperature up to 50 Mrads. The close rate was 1 Mrad/hr. After irradiation, the unreacted monomer was extracted with acetone. Polymer conversion versus $D/D_{50}$ is plotted as dots in the FIGURE. $D_{50}$ is the dose required for 50% polymer conversion. $G(-m)$, number of monomer reacted per 100 eV was determined from the slope of the plot of dots in the FIGURE. The $G(-m)$ for 1PPAPS is compared with PTS in Table 3.

THERMAL POLYMERIZATION

Two techniques were used. (1) Thermal annealing: 0.5 g of 1PPAPS was annealed at 80.6° C. for different periods of time. After annealing, the polymer conversion was determined by extracting unreacted monomer with acetone. Polymer conversion versus $t/t_{50}$ is plotted as triangles in the FIGURE. $t_{50}$ is the time required for 50% polymer conversion. (2) DSC: 10 mg of 1PPAPS was annealed in a differential scanning calorimeter at 100°, 120°, 130°, 135° and 140° C. Polymer conversion at time "t" was determined by taking a ratio of the area under the curve up to time "t" to that under the whole curve for the 120° C. DSC curve. A plot of polymer conversion versus $t/t_{50}$, where $t_{50}$ is time required for 50 percent polymerization from the 120° C. isothermal curve, is shown by a solid line in the FIGURE.

Time required for the maximum rate, $t_{max}$ of polymerization was noted from the peak position of DSC exotherms. A plot of $\ln(t_{max})$ versus $1/T$ where T is the absolute temperature yielded a straight line. The slope which gives the activation energy of polymerization was 94 kJ/mole for 1PPAPS.

1PPAPS was also annealed in DSC at 2.5, 5, 10° and 20° C./min heating rate. 1PPAPS polymerizes exothermically yielding a heat of polymerization of 138 kJ/mole.

The activation energy and the heat of polymerization for 1PPAPS are compared with PTS in Table 3.

TABLE 3

| Property | 1PPAPS | PTS |
|---|---|---|
| max (nm) | 600 | 570 |
| G(−m) initial | 140 | 40 |
| Δ Ep (kJ/mol) | 94 ± 6 | 94 ± 3 |
| Δ Hp (kJ/mol) | 178 ± 6 | 152 ± 4 |

EXAMPLE 13—OTHER ACETYLENIC COMPOUNDS WITH CHROMOPHORES

Acetylenic compounds are also prepared from the chromophoric reagents shown or named in the first column of Table 4 by reaction with the acetylenic reagents shown in the second column of Table 4. Products for some of these reactions are named below for the simplest case (n=1).

TABLE 4

| Ex. | Chromophoric Reactant | Acetylenic Reactant | Name R—CH$_2$—C C—CH$_2$—R |
|---|---|---|---|
| 13 | sodium naphthonate | $[C{\equiv}C{-}(CH_2)_n{-}Br]_2$ | 2,4-Hexadiyn-1,6-bis (1-aminonaphthalene-4-sulfonate) |
| 14 | Alizarin Red | $[C{\equiv}C{-}(CH_2)_n{-}Cl]_2$ | 2,4-Hexadiyn-1,6-bis sulfonate of alizarin red |
| 15 | Coumarin 343 | $[C{\equiv}C{-}(CH_2)_n{-}OH]_2$ | 2,4-Hexadiyn-1,6-bis ester of coumarin 343 |
| 16 | 3-(4-dimethylamino-1-naphthylazo)-4-methoxybenzenesulfonic acid | $[C{\equiv}C{-}(CH_2)_n{-}OH]_2$ | 2,4-Hexadiyn-1,6-bis [3-(4-dimethylamine-1-naphthylazo)-4-methoxybenzene sulfonate] |
| 17 | Nitrosine | $[C{\equiv}C{-}(CH_2)_n{-}COCl]_2$ | 2,4-Hexadiyn-1,6-bis (nitrosinamide) |
| 18 | Sudan III | $[C{\equiv}C{-}(CH_2)_n{-}COCl]_2$ | 2,4-Hexadiyn-1,6-bis amide of Sudan III |
| 19 | H$_2$N—⟨○⟩—N=N—⟨○⟩ | $[C{\equiv}C{-}(CH_2)_n{-}COCl]_2$ | 2,4-Hexadiyn-1,6-bis (p-phenylazophenyl amide) |
| 20 | H$_2$N—⟨○⟩—N=N—⟨○⟩—N=N—⟨○⟩ (with CH$_3$, CH$_3$) | $[C{\equiv}C{-}(CH_2)_n{-}COCl]_2$ | 2,4-Hexadiyn-1,6-bis (p-phenylazotolyl azotolylamide) |
| 21 | H$_2$N—(naphthyl)—N=N—⟨○⟩ | $[C{\equiv}C{-}(CH_2)_n{-}COCl]_2$ | 2,4-Hexadiyn-1,6-bis (p-phenylazonaphthyl 4-amide) |
| 22 | CH$_3$—(CH=CH)$_m$—COOH, m about 7-15 | $[C{\equiv}C{-}(CH_2)_n{-}OH]_2$ | 2,4-Hexadiyn-1,6-bis (methylheptavinylic carboxylate) |
| 23 | HO—SO$_2$⟨○⟩N=N⟨○⟩N(CH$_3$)$_2$ | $[C{\equiv}C{-}(CH_2)_n{-}OH]$ | 2,4-Hexadiyn-1,6-bis sulfonate of methyl-orange |

TABLE 4-continued

| Ex. | Chromophoric Reactant | Acetylenic Reactant | Name R—CH$_2$—C C—CH$_2$—R |
|---|---|---|---|
| 24 | H$_2$N—⌬—HC=CH—⌬—NO$_2$ | [C≡C—(CH$_2$)$_n$—COCl]$_2$ | 2,4-Hexadiyn-1,6-bis (p-nitrostilbene-4-amide) |
| 25 | H$_2$N—⌬—N=N—⌬—NO$_2$ | [C≡C—(CH$_2$)$_n$—COCl]$_2$ | 2,4-Hexadiyn-1,6-bis (p-nitrophenylazo phenylamide) |
| 26 | H$_2$N—⌬—N=N—(naphthyl) | [C≡C—(CH$_2$)$_n$—COCl]$_2$ | 2,4-Hexadiyn-1,6-bis (naphthylazo-4-phenyl-4-amide) |
| 27 | H$_2$N—[⌬—N=N]$_m$—⌬  m = 2,3,4, etc. | [C≡C—(CH$_2$)$_n$—COCl]$_2$ | 2,4-Hexadiyn-1,6-bis [phenyl-bis(azophenyl)-4-amide] |
| 28 | CH$_3$—(CH=CH)$_m$—COOH  m at least 6 | [C≡C—(CH$_2$)$_n$—CH$_2$OH]$_2$ | 2,4-Hexadiyn-1,6-bis (methyl hexavinylic carboxylate) |
| 29 | HO—⌬—N=N—(naphthyl) | [C≡C—(CH$_2$)$_n$COCl]$_2$ | 2,4-Hexadiyn-1,6-bis (4-naphthylazo-p-phenyl carboxylate) |
| 30 | HO—(naphthyl)—N=N—⌬ | [C≡C—(CH$_2$)$_n$COCl]$_2$ | 2,4-Hexadiyn-1,6-bis (p-phenylazo-4-naphthyl carboxylate) |

What is claimed is:

1. An indicator device comprising a substrate impregnated with an acetylenic compound having color in the visible spectrum and being active to polymerization on exposure to temperature or actinic radiation comprising an acetylenic portion having at least two conjugated acetylenic unsaturations and being capable of polymerization in the solid state, and at least one chromophore portion absorbing light in the visible spectrum.

2. The indicator device of claim 1 wherein said acetylenic compound is of the formula $$Q-(CH_2)_n-C\equiv C-C\equiv C-(CH_2)_n-R$$

wherein at least one of Q and R is a chromophoric substituent absorbing light in the visible spectrum and n is an integer from 1 to 10.

3. The indicator device of claim 2 wherein Q and R each contain azo chromophores.

4. The indicator device of claim 3 wherein Q and R are each

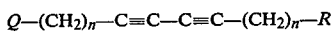

5. The indicator device of claim 4 wherein n is 1 to 4.
6. The indicator device of claim 3 wherein Q and R are each

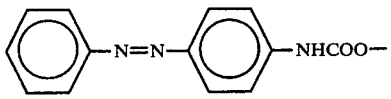

7. The indicator device of claim 6 wherein n is 1 to 4.
8. The indicator device of claim 7 wherein n is 1.
9. In a process which comprises applying to a perishable product an integral indicator of history of exposure to time-temperature or to radiation comprising at least one acetylenic compound having at least two conjugated acetylene groups per molecule, the improvement wherein the at least one acetylenic compound comprises at least one acetylenic compound having color in the visible spectrum and being active to polymerization on exposure to temperature or actinic radiation comprising an acetylenic portion having at least two conjugated acetylenic unsaturations and being capable of polymerization in the solid state, and at least one chromophore portion absorbing light in the visible spectrum.

10. The process of claim 9 wherein said acetylenic compound is of the formula $$Q-(CH_2)_n-C\equiv C-C\equiv C-(CH_2)_n-R$$

wherein at least one of Q and R is a chromophoric substituent absorbing light in the visible spectrum and n is an integer from 1 to 10.

11. The process of claim 10 wherein Q and R each contain azo chromophores.

12. The process of claim 11 wherein Q and R are each

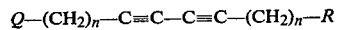

13. The process of claim 12 wherein n is 1 to 4.
14. The process of claim 11 wherein Q and R are each

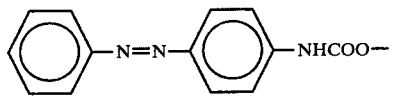

15. The process of claim 14 wherein n is 1 to 4.
16. The process of claim 15 wherein n is 1.

17. In a perishable product having applied thereto an integral indicator of history of exposure to time-temperature or to radiation comprising at least one acetylenic compound having at least two conjugated acetylene groups per molecule, the improvement wherein the at least one acetylenic compound comprises at least one acetylenic compound having color in the visible spectrum and being active to polymerization on exposure to temperature or actinic radiation comprising an acetylenic portion having at least two conjugated acetylenic unsaturations and being capable of polymerization in the solid state, and at least one chromophore portion absorbing light in the visible spectrum.

18. The perishable product of claim 16 wherein said acetylenic compound is of the formula

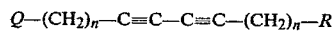

wherein at least one of Q and R is a chromophoric substituent absorbing light in the visible spectrum and n is an integer from 1 to 10.

19. The perishable product of claim 18 wherein Q and R each contain azo chromophores.

20. The perishable product of claim 19 wherein Q and R are each

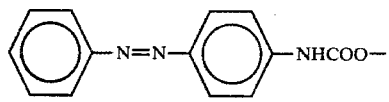

21. The perishable product of claim 20 wherein n is 1 to 4.

22. The perishable product of claim 21 wherein Q and R are each

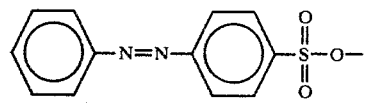

23. The perishable product of claim 22 wherein n is 1 to 4.

24. The perishable product of claim 23 wherein n is 1.